United States Patent [19]

Pankuch et al.

[11] Patent Number: 5,733,118
[45] Date of Patent: Mar. 31, 1998

[54] DENTAL IMPRESSION TRAY

[76] Inventors: John Pankuch, 1534 Georgetown Dr., Bloomfield Hills, Mich. 48304; Carl Irving Schwartz, 9413 Burning Tree La., Grand Blanc, Mich. 48439

[21] Appl. No.: 600,245

[22] Filed: Feb. 12, 1996

[51] Int. Cl.$^6$ .................................................... A61C 9/00
[52] U.S. Cl. ................................................ 433/38; 433/37
[58] Field of Search ................................ 433/34, 37, 38, 433/39, 45, 47, 48, 71

[56] References Cited

U.S. PATENT DOCUMENTS

| | | |
|---|---|---|
| 55,465 | 6/1866 | Buttles . |
| 1,583,928 | 5/1926 | Hollander et al. ................. 433/47 |
| 1,606,069 | 11/1926 | Freedman et al. ................. 433/47 |
| 1,608,632 | 11/1926 | Strusser .......................... 433/45 |
| 1,611,201 | 12/1926 | Kidder ........................... 433/45 |
| 2,657,461 | 6/1953 | Sweeney . |
| 2,963,786 | 12/1960 | Browning ........................ 433/37 |
| 3,505,995 | 4/1970 | Greenberg ....................... 433/37 |
| 4,085,507 | 4/1978 | Lehn et al. . |
| 4,200,981 | 5/1980 | Fine ............................. 433/60 |
| 4,204,323 | 5/1980 | Neubert et al. . |
| 4,283,173 | 8/1981 | Browne et al. . |
| 4,368,040 | 1/1983 | Weissman ........................ 433/37 |
| 4,449,927 | 5/1984 | Taylor .......................... 433/45 |
| 4,689,010 | 8/1987 | Wolfe . |
| 4,907,966 | 3/1990 | Kesling . |
| 5,316,474 | 5/1994 | Robertson . |
| 5,554,024 | 9/1996 | Ueda ............................ 433/37 |
| 5,636,985 | 6/1997 | Simmen et al. ................... 433/37 |

FOREIGN PATENT DOCUMENTS

| 2316589 | 10/1973 | Germany ......................... 433/37 |
|---|---|---|

*Primary Examiner*—Ralph Lewis
*Attorney, Agent, or Firm*—Brooks & Kushman, P.C.

[57] ABSTRACT

A dental impression tray contoured to fit over at least a portion of a patient's dentition is provided. The dental impression tray includes a wall portion and an elongate rib adapted to extend along the wall portion. The elongate rib and wall define a channel sufficiently elongate with respect to the portion of the patient's dentition to interfit with an impression material during an impression of the portion of the patient's dentition to hold the impression material more securely in the tray.

14 Claims, 2 Drawing Sheets

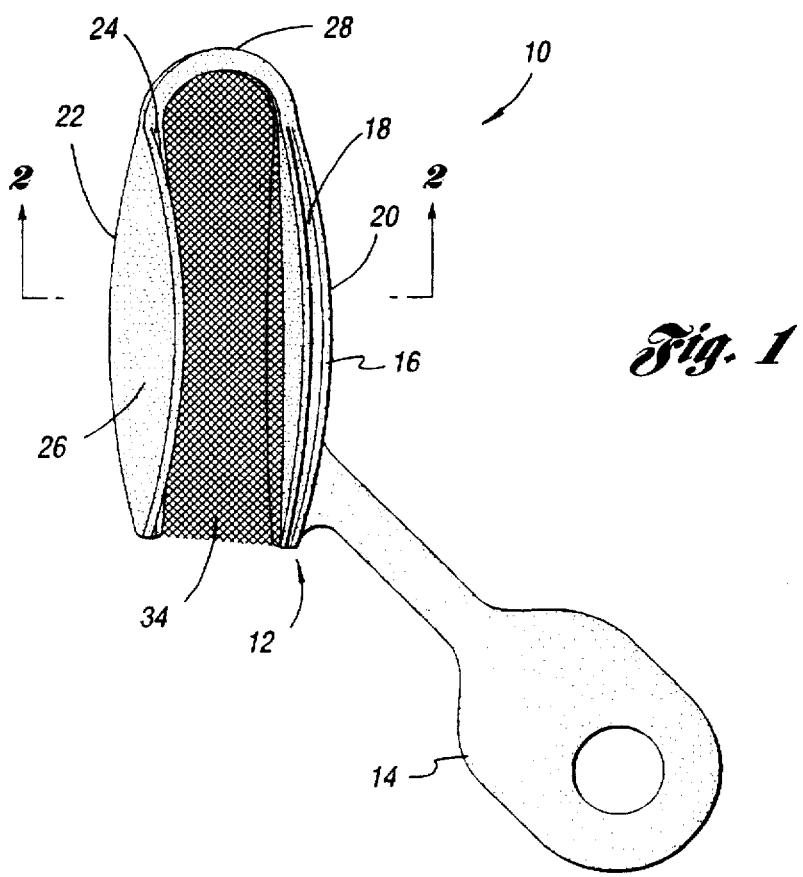
Fig. 1
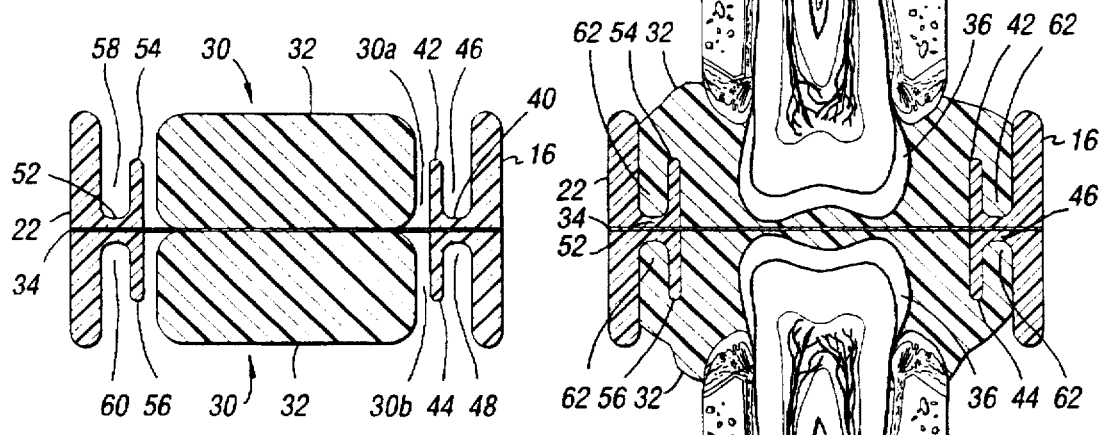
Fig. 2
Fig. 3

DENTAL IMPRESSION TRAY

TECHNICAL FIELD

The present invention relates to dental impression trays for obtaining an impression of a patient's dentition.

BACKGROUND ART

Conventional dental trays generally include a tray portion anatomically contoured to fit over at least a portion of a patient's upper and/or lower dentition. Trays may be designed to cover different portions of a patient's dentition. For example, a full arch tray may be designed to take an impression of the entire dentition of a patient. Alternatively, the tray may be designed to take an impression of either the right half or left half of the patient's dentition. Finally, trays may be designed to take an impression of either the anterior or posterior portions of a patient's dentition.

To take an impression, the tray portion is loaded with a suitable impression material and placed opposite the desired portion of the dentition. The patient then bites into the impression material to form an impression of the dentition in the material. The dental tray is then removed from the patient's mouth, and the impression material is allowed to set. After the impression sets, in is used as a mold for forming a model of the dentition.

Dental impression trays can be used to take impressions of the upper or lower dentitions singly, or both simultaneously. Trays that take impressions of both dentitions simultaneously usually contain a membrane or mesh separating the tray portion into top and bottom halves. Impression material is placed both above and below the membrane, and the patient, upon biting on the impression material, leaves an impression in both portions of the impression material, both above and below the mesh.

A problem encountered with conventional dental impression trays is that the impression material tends to move with respect to the tray walls after the impression is taken and before the impression material has set. After the impression is taken, the soft impression material tends to separate from the tray walls. In addition, the impression material tends to lift out of the trays when the impression material is removed from the patient's teeth. These movements can distort the impression.

Additional distortion can arise if the tray is too flexible. An excessively flexible tray may bend out, away from the teeth, when the patient is making the impression. Upon removal from the patient's teeth, memory in the tray material may cause the tray to contract and bend back inward, potentially distorting the impression.

DISCLOSURE OF INVENTION

Accordingly, the principle object of the present invention is to provide a dental impression tray with a rib at least partially defining a channel for interfitting an impression material with the tray.

Another object of the present invention to provide a dental tray having elongate ribs on both the buccal and lingual walls of the impression device.

Another object of the present invention is to provide a dental impression tray manufactured from glass filled nylon for superior rigidity, thereby improving the accuracy of a resulting dental impression.

In accordance with these objects, a dental impression tray contoured to fit over at least a portion of a patient's dentition is provided. In the preferred embodiment, the dental impression tray comprises a wall portion and an elongate rib adapted to extend along the wall portion. The elongate rib and wall define a channel sufficiently elongate with respect to the portion of the patient's dentition to interfit with an impression material during an impression of the portion of the patient's dentition.

These and other objects, features and advantages will be readily apparent upon consideration of the following detailed description in conjunction with the accompanying drawings.

BRIEF DESCRIPTION OF DRAWINGS

FIG. 1 is a perspective view of a dental impression tray incorporating the present invention;

FIG. 2 is a cross-sectional view of the dental tray shown in FIG. 1, taken along line 2—2;

FIG. 3 is the same cross-sectional view of FIG. 2 during an impression of at least a portion of a patient's dentition;

BEST MODE FOR CARRYING OUT THE INVENTION

Figure 4:
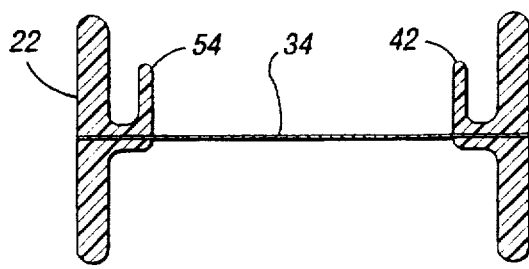
FIG. 4 is a cross-sectional view of an alternative embodiment of the present invention.

Referring to the drawings, FIG. 1 shows a perspective view of a dental impression tray 10 incorporating the present invention. The tray 10 is adapted for use in obtaining an impression of the posterior, or bicuspid and molar, part of both the upper and lower dentitions, and is accordingly referred to as a posterior dental impression tray. FIG. 2 shows a cross-sectional view of the posterior dental impression tray 10 of FIG. 1.

Referring first to FIG. 1, the posterior dental impression tray 10 includes a tray portion 12 and a handle 14 connected thereto. Handle 14 is preferably shaped and contoured to conform to the shape and contour of a human thumb; for easy handling. The tray portion 12 and handle 14 are integrally molded of a suitable material. The preferred material for the present invention is 33% glass filled nylon, but 5% to 60% glass filled nylon is acceptable. This glass filled nylon is preferred to common plastics because it provides enhanced structural rigidity, decreasing the potential for distortion in the dental impression which the dental impression tray is used to make.

Referring now to FIGS. 1 and 2, tray portion 12 includes buccal wall 16 which has an inner surface 18 and an outer surface 20. Tray 12 also includes lingual wall 22 which has an inner surface 24 and an outer surface 26. The buccal wall 16 and lingual wall 22 are bridged together by a bridging member 28.

The buccal wall 16 and lingual wall 22 define a cavity 30 into which the impression material 32 is placed. A mesh 34 divides the cavity into two halves, 30a and 30b. The mesh 34 allows for taking an impression of both the upper and lower dentitions of a patient simultaneously. The impression material 32 is made of any suitable conventional elastomeric material and is loaded into the cavity portions 30a and 30b while in a soft condition. The mesh 34 is formed from any suitable material, such as gauzes and extends horizontally through the cavity. The mesh is preferably made from a material having a high strength to weight ratio and is assembled as part of the dental impression tray 10 during the molding operation. While preferable, it should be noted that the present invention may be utilized without mesh 34, depending upon the specific design of the particular dental impression tray employed.

Still referring to FIGS. 1 and 2, the buccal wall 16 of tray 12 includes a horizontally oriented buccal rib 40. The buccal rib 40 has a first buccal lip 42 and a second buccal lip 44. Together with the buccal wall 16 and buccal rib 40, the first buccal lip 42 defines a first buccal channel 46, and the second buccal lip 44 defines a second buccal channel 48. Buccal rib 40 and buccal lips 42 and 44, and buccal channels 46 and 48 formed thereby, preferably extend along the entire length of buccal wall 16. However, buccal rib 40 and buccal lips 42 and 44 may be formed along any suitable length of buccal wall 16.

Similarly, the lingual wall 22 of tray 12 includes a horizontally oriented lingual rib 52. The lingual rib 52 includes first and second lingual lips 54 and 56. Together with the lingual wall 22 and lingual rib 52, the lingual lips 54 and 56 define first and second lingual channels 58 and 60, respectively. Both the buccal 40 and lingual 52 ribs are generally parallel to the mesh 34. Once again, lingual rib 52 and lingual lips 54 and 56, and lingual channels 58 and 60 formed thereby, preferably extend along the entire length of lingual wall 22. However, lingual rib 52 and lingual lips 54 and 56 may be formed along any suitable length of lingual wall 22.

Still referring to FIGS. 1 and 2, in use, suitable impression material 32 is loaded into the upper and lower sections 30a and 30b of cavity 30. Tray 10 is grasped by handle 14 and situated opposite to or between the dentition area of the patient. Referring next to FIG. 3, which depicts a cross-section of tray 10 during a dental impression, the patient bites into impression material 32 to form an impression of the dentition therein. After the impression material 32 partially sets, it is removed from the patient's teeth 36 leaving an impression. The impression material is then allowed to fully set, whereupon it can be used as a mold.

As noted, when conventional dental impression trays are used, the impression can become distorted. As mentioned above, the present invention addresses this problem in part through the use, preferably, of a more rigid material. In that regard, 33% glass filled nylon is the material of choice for the preferred embodiment of the present invention. The present invention also addresses the distortion problem though the use of a means for interfitting the impression material with the tray so that the impression material is not lifted away from the tray upon removal of the patient's dentition.

More specifically, referring again to FIG. 3, when dental tray 10 is placed inside a patient's mouth, and the patient bites into the impression material 32, portions 62 of the impression material 32 flow over the buccal and lingual lips 42, 44, 54 and 56 into the buccal and lingual channels 46, 48, 58 and 60. The portions 62 of the impression material 32 that flow into the buccal and lingual channels 46, 48, 58 and 60 create an interfit between the impression material 32 and tray 12. This interfit keeps the impression material 32 in place and inhibits the material 32 from moving away from buccal wall 16 and lingual wall 22 when the patient's teeth are removed from the impression material 32, thereby improving the accuracy of the impression.

As previously noted, buccal and lingual ribs 40 and 52 and buccal and lingual lips 42, 44, 54 and 56 may be formed along any length of buccal and lingual walls 16 and 22. However, buccal and lingual channels 46, 48, 58 and 60 should be sufficiently elongate with respect to the patient's dentition to allow the interfitting described above.

Figure 5:
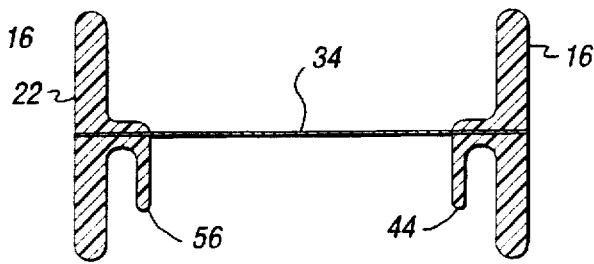
FIG. 5 is a cross-sectional view of an alternative embodiment of the present invention.

While the preferred embodiment of the present invention incorporates two buccal lips 42 and 44, and two lingual lips 54 and 56, creating four channels, 46, 48, 58 and 60, it should be appreciated that one may choose to employ only a single lip and still incorporate the present invention. For example, FIGS. 4 and 5 show cross-sections of embodiments having a single buccal lip and a single lingual lip. In FIG. 4, the lips are directed upward, and in FIG. 5 the lips are directed downward.

Figure 6:
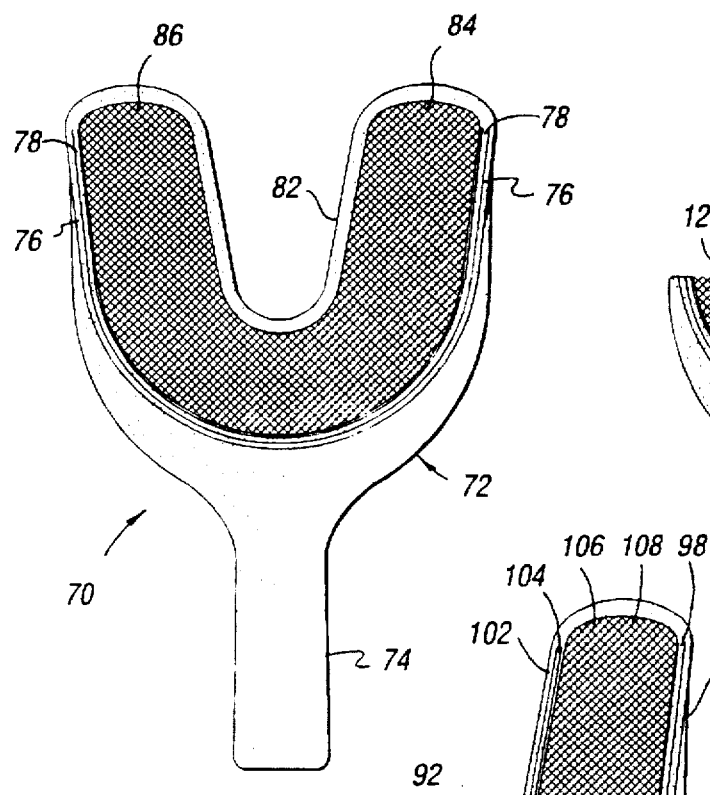
FIG. 6 is a top plan view of a full arch dental impression tray incorporating the present invention.

The invention may also be incorporated in dental impression trays for taking impressions of other parts of the dentition. Referring to FIG. 6, another embodiment of the dental impression tray in accordance with the invention is illustrated. Dental impression tray 70 is adapted for use in obtaining an impression of the entire jaw, and is accordingly referred to as a full arch dental tray. Full arch dental impression tray 70 includes a tray portion 72 and a handle 74. As with posterior dental impression tray 10, the tray portion 72 and handle 74 of full arch dental impression tray 70 is preferably made of 33% glass filled nylon. Handle 74 is preferably shaped and contoured to fit the shape of the contour of a human thumb for easy handling.

Tray 72 includes a buccal wall 76 having a buccal rib 78. Buccal rib 78 functions similarly to buccal rib 40 and lingual rib 52 of the tray portion 12 of the posterior dental impression tray 10 described above. Accordingly, the details of the operation will not be restated here. Tray 72 also includes a lingual wall 82. In this embodiment, the lingual wall 82 does not include a lingual rib. It has been found that for full arch dental impression tray 70, a lingual rib is not needed. It should be recognized, however, that a lingual rib could be included.

Buccal wall 76 and lingual wall 82 define a cavity 84 which is divided into two portions by a mesh 86 in a manner similar to that described above for cavity 30 and mesh 34 of the posterior dental impression tray 10. In operation, dental impression material can be placed into both halves of cavity 84, and a dental impression can be taken in a manner similar to that described above.

Figure 7:
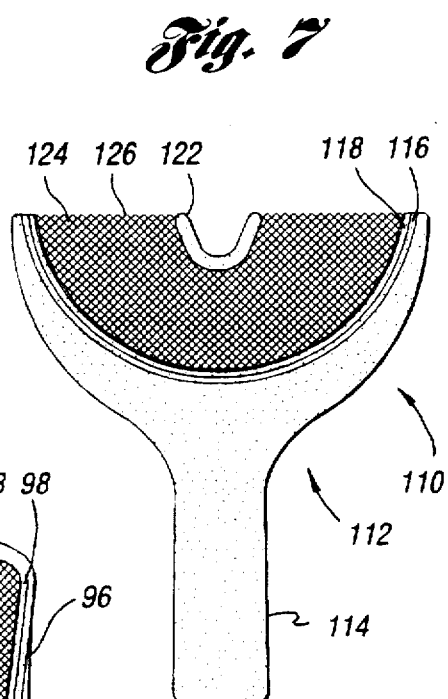
FIG. 7 is a top plan view of a quadrant dental impression tray incorporating the present invention.
Figure 8:
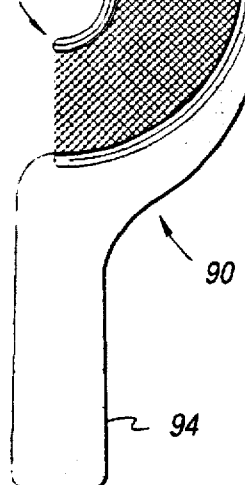
FIG. 8 is a top plan view of an anterior dental impression tray incorporating the present invention.

The present invention may be applied in the construction of other dental impression trays as well. In this respect, FIG. 8 illustrates a dental impression tray used for taking the impression of either the right or left half of a patient's dentition. It is referred to as a quadrant dental impression tray 90. Similarly, FIG. 7 shows a dental impression tray incorporating the present invention for use in taking an impression of the anterior, or incisor and cuspid, portion of a patient's dentition. It is referred to as an anterior dental impression tray 10.

Quadrant dental impression tray 90 includes a tray portion 92, a handle 94, a buccal wall 96 having buccal rib 98, and lingual wall 102 having a lingual rib 104. The buccal wall 96 and lingual wall 102 define a cavity 106 which can be divided to two portions by a mesh 108. Anterior dental impression tray 110 includes a tray portion 112, a handle 114, a buccal wall 116 having a buccal rib 118, and a lingual wall 122. The buccal wall 116 and lingual wall 122 define a cavity 124 which has a mesh 126 dividing it into two portions.

As is readily apparent from the foregoing detailed description, the present invention provides an improved dental impression tray that prevents contraction of the impression material and holds the impression material more securely in the tray. In that regard, the present invention provides a dental impression tray with a rib at least partially defining a channel for interfitting an impression material with the tray.

More specifically, the present invention provides a dental tray having elongate ribs on both the buccal and lingual walls of the impression device. The present invention also provides a dental impression tray manufactured from glass filled nylon for superior rigidity, thereby improving the accuracy of a resulting dental impression.

It is to be understood that the present invention has been described in an illustrative manner and the terminology which has been used is intended to be in the nature of words of description rather than of limitation. Obviously, many modifications and variations of the present invention are possible in light of the above teachings. Therefore, it is also to be understood that, within the scope of the following claims, the invention may be practiced otherwise than as specifically described.

What is claimed is:

1. A dental impression tray contoured to fit over at least a portion of a patient's dentition, the dental impression tray comprising:

first and second spaced apart walls defining a receiving cavity for receiving an impression material;

a horizontally oriented rib extending from the first wall into the receiving cavity;

a first lip connected at one end to the rib and extending from the rib generally parallel with the first wall, wherein the first wall, the rib, and the first lip define a first channel for receiving a portion of the impression material which flows over the first lip from the receiving cavity into the first channel during an impression of the portion of the patient's dentition such that the impression material interfits with the dental impression tray; and a mesh located within the receiving cavity, wherein the mesh is connected to the second wall and extends across the receiving cavity through the rib and is connected to the first wall thereby dividing the receiving cavity into multiple portions.

2. The dental impression tray of claim 1 wherein the first channel extends substantially along the first wall.

3. The dental impression tray of claim 1 further comprising a second lip connected at one end to the rib and extending from the rib opposite of the first lip and generally parallel with the first wall, wherein the first wall, the rib, and the second lip define a second channel for receiving a portion of the impression material which flows over the second lip from the receiving cavity into the second channel during an impression of the portion of the patient's dentition.

4. The dental impression tray of claim 3 wherein the second channel extends substantially along the first wall.

5. The dental impression tray of claim 3 wherein the first rib, the first lip, and the second lip have a generally T-shaped cross section.

6. The dental impression tray of claim 1 wherein the first and second walls, the rib, and the first lip are comprised of glass filled nylon.

7. The dental impression tray of claim 1 wherein the first and second walls, the rib, and the first lip are manufactured from approximately 5%–60% glass filled nylon.

8. The dental impression tray of claim 1 wherein the rib and the first lip have a generally L-shaped cross-section.

9. The dental impression tray of claim 1 wherein the first and second walls are bridged together at one end by a bridging member.

10. A dental impression tray contoured to fit over at least a portion of a patient's dentition, the dental impression tray comprising:

a buccal wall having an inner surface;

a lingual wall having an inner surface facing the inner surface of the buccal wall, the inner surfaces of the buccal and lingual walls defining a receiving cavity adapted to receive a dental impression material;

a horizontally oriented buccal rib extending from the inner surface of the buccal wall into the receiving cavity;

a first buccal lip connected at one end to the buccal rib and extending from the buccal rib generally parallel with the buccal wall, wherein the buccal wall, the buccal rib, and the first buccal lip define a first buccal channel;

a second buccal lip connected at one end to the buccal rib and extending from the buccal rib opposite of the first buccal lip and generally parallel with the buccal wall, wherein the buccal wall, the buccal rib, and the second buccal lip define a second buccal channel;

a horizontally oriented lingual rib extending from the inner surface of the lingual wall into the receiving cavity;

a first lingual lip connected at one end to the lingual rib and extending from the lingual rib generally parallel with the lingual wall, wherein the lingual wall, the lingual rib, and the first lingual lip define a first lingual channel; and a second lingual lip connected at one end to the lingual rib and extending from the lingual rib opposite of the first lingual lip and generally parallel with the lingual wall, wherein the lingual wall, the lingual rib, and the second lingual lip define a second lingual channel.

11. The dental impression tray of claim 10 wherein the buccal and lingual ribs are formed substantially along the inner surfaces of the buccal and lingual walls, respectively.

12. The dental impression tray of claim 10 further comprising a mesh located within the receiving cavity, wherein the mesh extends across the receiving cavity through the buccal and lingual ribs and is connected to the inner surfaces of the buccal and lingual walls thereby dividing the receiving cavity into upper and lower portions.

13. The dental impression tray of claim 10 wherein the buccal and lingual walls, lips, and ribs are comprised of glass filled nylon.

14. The dental impression tray of claim 10 wherein the buccal and lingual walls, lips, and ribs are manufactured from approximately 5%–60% glass filled nylon.

* * * * *